United States Patent [19]
Holme et al.

[11] Patent Number: 5,696,100
[45] Date of Patent: Dec. 9, 1997

[54] METHOD FOR CONTROLLING O-DESULFATION OF HEPARIN AND COMPOSITIONS PRODUCED THEREBY

[75] Inventors: Kevin R. Holme, Alameda; Weisheng Liang, San Francisco, both of Calif.; Patrick N. Shaklee, Waunakee, Wis.

[73] Assignee: Glycomed Incorporated, Alameda, Calif.

[21] Appl. No.: 384,298

[22] Filed: Feb. 6, 1995

Related U.S. Application Data

[63] Continuation of Ser. No. 300,291, Sep. 1, 1994, abandoned, which is a continuation-in-part of Ser. No. 210,847, Mar. 21, 1994, abandoned, which is a continuation-in-part of Ser. No. 994,804, Dec. 22, 1992, Pat. No. 5,296,471.

[51] Int. Cl.$^6$ .................................................. A61K 31/725
[52] U.S. Cl. .................................. 514/56; 514/54; 536/21
[58] Field of Search .............................. 514/56, 54; 536/21

[56] References Cited

U.S. PATENT DOCUMENTS

| | | | |
|---|---|---|---|
| 4,613,665 | 9/1986 | Larm | 536/21 |
| 4,774,231 | 9/1988 | Petitou et al. | 514/53 |
| 4,954,637 | 9/1990 | Nitecki et al. | 548/546 |
| 4,990,502 | 2/1991 | Lormeau et al. | 514/56 |
| 5,010,063 | 4/1991 | Piani et al. | 514/56 |
| 5,104,860 | 4/1992 | Piani et al. | 514/56 |
| 5,236,910 | 8/1993 | Egidio et al. | 514/56 |
| 5,280,016 | 1/1994 | Conrad | 514/56 |

FOREIGN PATENT DOCUMENTS

| | | | |
|---|---|---|---|
| 0413248-A1 | 2/1991 | European Pat. Off. . | |
| 0 454 220 A1 | 10/1991 | European Pat. Off. | C07H 15/04 |
| 0483733-A1 | 5/1992 | European Pat. Off. . | |
| 0 489 647 A2 | 6/1992 | European Pat. Off. | C08B 37/00 |
| 0 557 887 A2 | 9/1993 | European Pat. Off. | C08B 37/10 |
| 0 565 862 A2 | 10/1993 | European Pat. Off. | C08B 37/10 |
| 0 565 863 A2 | 10/1993 | European Pat. Off. | C08B 37/10 |
| 8705457 | 4/1987 | France | C08B 37/10 |
| WO 91/15216 | 10/1991 | WIPO . | |
| WO 92/01003 | 1/1992 | WIPO . | |
| WO 92/17187 | 10/1992 | WIPO . | |
| WO 92/18545 | 10/1992 | WIPO . | |
| WO 93/19096 A1 | 9/1993 | WIPO . | |
| WO 94/02107 | 2/1994 | WIPO . | |

OTHER PUBLICATIONS

Article by Guo, et al., entitled "The Disaccharide Composition of Heparins and Heparan Sulfates" published by *Academic Press, Inc.* Analytical Biochemistry, 176:96–104 (1989).

Jaseja, et al., "Novel Regio–and Stereoselective Modifications of Heparin in Alkaline Solution. Nuclear Magnetic Resonance Spectroscopic Evidence" published by *Can. J. Chem.* 67:1449–1456 (1989).

Rej, et al., "Base–catalyzed Conversion of the a–L–iduronic acid 2–sulfate Unit of Heparin into a Unit of a–L–galacturonic Acid, and Related Reactions" published by Elsevier Science Publishers B.V., (1989).

Gershenson et al., "Tyrosine Transaminase Induction by Dexamethasone in a New Rat Liver Cell Line," Science, 170:859–861 (1970).

Purkerson et al., "N–Desulfated/Acetylated Heparin Ameliorates the Progression of Renal Disease in Rats with Subtotal Renal Ablation," J. Clin. Invest., 81:69–74 (1988).

Sache et al., "Partially N–Desulfated Heparin as a Non–anticoagulant Heparin: Some Physico–Chemical and Biological Properties," Thrombosis Res. 55:247–258 (1989).

Bienkowski et al., "Structural Characterization of the Oligosaccharids Formed by Depolymerization of Heparin with nitrous Acid," J. Biol. Chem., 260(1):356–363 (1985).

Folkman et al., "Angiogenesis Inhibition and Tumor Regression Caused by Heparin or a Heparin Fragment in the Presence of Cortisone," Science, 221:719–725 (1983).

Kohler et al., "Continuous cultures of fused cells secreting antibody of predefined specificity," 256:495–297 (1975).

Liu et al., Adverse effects of alkali and acid on the anticoagulant potency of heparin, evaluated with methl 2–deoxy–2–sulfamino–α–D–glucopyranoside 3–sulfate as a model compound, Carbohyd. Res., 228:29–36 (1992).

Kosakai et al., "Ester Sulfates in Sulfated Oligosaccharides from the Deamination Prodcts of Procine Heparin and Whale Heparin," Chemistry and Biology of Heparin, 97–104 (1981).

Liu, et al., "Adverse Effects of Alkali and Acid on the Anticoagulant Potency of Heparin, Evaluated with methyl 2–deoxy–2–sulfamino–α–D–Glucopryanoside 3–Sulfate as Model Compound" *Elsevier Science Publishers B.V.*, Amsterdam, Carbohydrate Research 228:29–36 (1992).

Fraidenraich et al., "Selective O–desulphation of Heparin in Triethylamine," *Elsevier Science Publishers, Ltd.,* Carbohydrate Polymers, pp. 111–114 (1991).

Mitchell et al., "Inhibitors of Angiogenesis" *Academic Press, Inc.,* pp. 139–148 (1992).

Hirsh et al., "Low Molecular Weight Heparin" *The Journal of the American Society of Hematology,* Blood, 79, No. 1:1–17 (1992).

Castellot, et al., "Heparin Potentiation of 3T3–Adipocyte Stimulated Angiogenesis: Mechanisms of Action on Endothelial Cells" *Journal of Cellular Physiology,* pp. 323–329 (1986).

Ishihara et al., "A Cell–Based Assay for Evaluating the Interaction of Heparin–like Molecules and Basic Fibroblast Growth Factor" *Academic Press, Inc.,* 202:310–315 (1992).

Irimura et al., *Biochemistry* (1986) 25:5322–5328.

Bar–Ner et al., *Blood* 70(2) (1987) pp. 551–557.

(List continued on next page.)

*Primary Examiner*—Herbert J. Lilling
*Attorney, Agent, or Firm*—Lyon & Lyon LLP

[57] ABSTRACT

Methods of making and using, as prophylactics or therapeutics for preventing or treating certain diseases including cancer, O-desulfated heparin compositions, preferably 2-O, 3-O desulfated heparin compositions, wherein the methods permit regulating the degree of 2-O, 3-O desulfation to produce compositions that are variably desulfated upto about and 75% desulfated at the 2-O and 3-O positions, respectively.

12 Claims, 3 Drawing Sheets

OTHER PUBLICATIONS

Rone et al., *Endocrinology* 127(6) (1990) pp. 2821–2828.

Stokes et al., *Lab Invest.* 63(5) (1990) pp. 657–668.

Velluz et al., C.R. Acad. Sci. Paris (1959) 247:1521–1523.

Conrad, "Structure of Heparan Sulfate and Dermatan Sulfate," Annals of N.Y. Academy of Sci. 556:18–28 (1989).

Ishihara et al., "A Cell–Based Assay for Evaluating the Internation of Heparin–like Molecules and Basic Fibroblast Growth Factor," Analytical Biochem. 202:310–315 (1992).

Inoue et al., "Selective N–Desulfation of Heparin with Dimethyl Sulfoxide Containing Water or Methanol," Carbohydrate Res., 46:87–95 (1976).

Fransson et al., "Relationship Between Anticoagulant Activity of Heparin and Susceptibility to Periodate Oxidation," FEBS Letters, 97:(1):119–123 (1979).

Casu et al., "Retention of Antilepemic Activity by Periodate–oxidized Non–anti–coagulant Heparins," Arzneim–Forsch/Drug Res. 36:(I):4:637–642 (1986).

Fransson et al., "Periodate Oxidation and Alkaline Degradation of Heparin–Like Related Glycans," Carbohyd. Res. 80:131–145 (1980).

Shaklee et al., "Hydrazinolysis of heparin and other glycosaminoglycans," Biochem J., 217:187–197 (1984).

Guo et al., "Analysis of Oligosaccharides from Heparin by Reversed–Phase Ion–Pairing High–Performance Liquid Chromatography[1]," Analyt. Biochem. 168:54–62 (1988).

Folkman et al., "Angiostatic Steroids—Method of Discovery and Mechanism of Action," Ann. Surg., 206:374–383 (1987).

Fendly et al., "Murine Monoclonal Antibodies Defining Neutralizing Epitopes on Tumor Necrosis Factor," Hybridoma, 6:359–370 (1987).

Lloyd et al., "Preparation of [35]Sulphamate Derivatives for Studies on Heparin Degrading Enzymes of Mammalian Origin," Biochem Pharma., 20:637–648 (1971).

Sobel et al., "Heparin Inhibition of von Willebrand Factor–dependent Platelet Function In Vitro and In Vivo," J. Clin. Invest. 87:1787–1793 (1992).

Rej et al., "Base–catalyzed conversion of the α–L–iduronic acid 2–sulfate unit of heparin into a unit of α–L–galacturonic acid, and related functions," Carbohyd. Res. 200:437–447 (1990).

Luben et al., "In Vitro Immunization as an Adjunct to the Production of Hybridomas Producing Antibodies against the Lymphokine Osteoclast Activating Factor," Molecular Immunol. 17:635–639 (1980).

Ayotte et al., "N.M.R. Spectroscopic Observations Related to the Function of Sulfate Groups in Heparin, Calcium Binding vs. Biological Activity," Carbohyd. Res. 145:267–277 (1986).

Charles et al., "Studies on Heparin. IV. Observations on the Chemistry of Heparin", Biochem. J. 30:1927–1933 (1936).

Reading "In Vitro Immunization for the Production of Antigen–Specific Lymphocyte Hybridomas," Methods in Enzymology, 121:18:27 (1986).

Boss et al., "An Improved In Vitro Immunization Procedure for the Production of Monoclonal Antibodies," Methods in Enzymology., 121:27–33 (1986).

Kelton, et al., "A Comparison of the Quantitative Bistocetin von Willebrand Factor Assay by Using Fresh and Fixed Platelets," Thromb. Res. 18:477–483 (1980).

Coyne, "Heparin—Past, Present and Future," Chemistry and Biology of Heparin, 9–17 (1981).

METHOD FOR CONTROLLING O-DESULFATION OF HEPARIN AND COMPOSITIONS PRODUCED THEREBY

This patent application is a continuation of U.S. patent application Ser. No. 08/300,291, filed Sep. 1, 1994 now abandoned, which is a continuation-in-part of Ser. No. 08/210,847, filed Mar. 21, 1994 now abandoned. Ser. No. 08/210,847 is a continuation-in-part of U.S. Ser. No. 08/994,804 filed Dec. 22, 1992, abn., U.S. Pat. No. 5,296,471, issued on Mar. 22, 1994. Priority is hereby claimed per 35 U.S.C. §120.

FIELD OF THE INVENTION

This invention relates to methods of making O-desulfated heparin compositions, preferably 2-O, 3-O desulfated heparin compositions, wherein the methods permit regulating the degree of 2-O, 3-O desulfation to produce compositions that can be variably desulfated including about 99% and 75% desulfated at the 2-O and 3-O positions, respectively. Such compositions, have significant anti-cancer activity in vivo, substantially lack anti-coagulant activity, inhibit platelet aggregation, exhibit reduced binding to bFGF, and have anti-angiogenic and heparanase inhibitory activity. The compositions are useful for treating various diseases, including cancer.

Abbreviations

The following abbreviations are used for monosaccharides or for monosaccharides residues included in oligomers: D-glucuronic acid=GlcA; L-iduronic acid=IdoA; D-glucosamine=$GlcNH_2$; N-acetyl-D-glucosamine=GlcNAc; D-glucosamine N-sulfate=GlcNS; 2,5-anhydromannose=Aman; 2,5-anhydromannitol=AManHh.

Abbreviations that are used to denote disaccharide residues obtained in the analysis of heparin compositions described herein are as follows: ISMS is defined as IdoA (2-sulfate)→AManH (6-sulfate); $GMS_2$ is defined as GlcA→AManH (3,6-disulfate); IS is defined as IdoA (2-sulfate)→AManH (6-sulfate)+IdoA (2-sulfate)→AManH.

In designating each saccharide residues below the appropriate abbreviation, the location of the O-linked sulfate residues is indicated by "S" and the number of the position of sulfation where the sulfate residue is linked to oxygen on the sugar residue. In the designations for heparin structure, also, the positions involved in the alpha and beta anomeric linkages are as those conventionally found in heparin, α (glucosamine→uronic) and β (uronic→glucosamine), and the D or L configurations as conventionally found pertains. The locations of the sulfates are shown below the abbreviation for the sugar to which they apply, thus, for example, IdoA—GlcNS
2S    6S refers to a disaccharide composed of L-iduronic acid and D-glucosamine N-sulfate-linked β(1–4) with sulfates connected respectively at the 2 and 6 positions of the sugar residues.

Background

Heparin

Heparin/heparan sulfate is a member of a class of polysaccharides known as glycosaminoglycans (GAG). These materials are copolymers of alternating hexosamine and aldouronic acid residues which are found in sulfated forms and are synthesized as proteoglycans. In the compositions of interest herein, heparan sulfate and heparin, the hexosamine which predominates is N-acetylated or N-sulfated glucosamine (GlcNAc and GlcNS). The aldouronic acid is mostly L-iduronic in heparin and mostly D-glucuronic acid in heparan sulfate. Heparan sulfate is commonly considered to have a higher proportion of glucuronic acid than heparin.

Problems of heterogeneity in preparations of heparan sulfate or heparin isolated from tissues make sharp distinctions difficult. Conventional heparin (used as an anticoagulant) has a molecular weight of 5–25 kd and is extracted as a mixture of various chain lengths by conventional procedures. These procedures involve autolysis and extraction of suitable tissues, such as beef or porcine lung, intestine, or liver, and removal of nonpolysaccharide components. The molecular weight of the chains in the extract is significantly lower than the 60–100 kd known to exist in the polysaccharide chains of the heparin proteoglycan synthesized in the tissue. The GAG moiety is synthesized bound to a peptide matrix at a serine or threonine residue through a tetrasaccharide linkage region of the sequence D-GlcA-D-Gal-D-Gal-D-Xyl→protein, which is then elongated at the D-GlcA residue with alternate additions of GlcNAc and GlcA. The polymer undergoes epimerization at certain of the GlcA residues to give IdoA, and subsequent sulfation.

Due to their chemical similarity, isolated "heparin" may contain considerable mounts of what might otherwise be classified as heparan sulfate.

Modified Desulfated Heparins

Several investigators have described the preparation of desulfated heparin. For instance, partially N-desulfated heparins are shown by Velluz, in *C. R. Acad. Sci. Paris* (1959) 247:1521, Sache, in Thrombosis Res. 55–247 (1989), and by Inoue in *Carbohyd. Res.* (1976) 46:87.

Other investigators have described the N-acetylation of N-desulfated heparin. See, Purkenson, *J. Clin. Invest.* (1986) 81:69; Inoue, *Carbohyd. Res.* (1976) 46:87; and Ayotte, *Carbohyd. Res.* (1986) 145:267–277.

Further, Jaseja, M. et al., have reported that alkaline treatment of heparin results in a sequence of specific transformations that involve the loss of 2-O-sulfate. See, *Can. J. Chem.* (1989) 67:1449–1456. These investigators studied the alkaline desulfation of beef lung heparin. The instant invention presents methods for realizing defined compositions of 2-O, 3-O desulfated heparin from a chemically less homogenous source of heparin, hog mucosal heparin.

Three different transformations were characterized by Jaseja, M. et al., above, depending on the reaction conditions. The first, lyophilization of a mildly alkaline (pH 11.2–11.5) solution of beef lung heparin caused the partial conversion of 2-O-sulfated IdoA residues to non-sulfated uronic acid residues possessing the α-L-gulo configuration, and a 2,3-oxirane functionality (characterized by resonances in the $^{13}$C-nmr spectrum at 53.5 and 54.0 ppm, and assigned to the C-2 and C-3 carbons of the new uronic acid residue). The conversion to the oxirane under these conditions is typically incomplete, with the highest reported conversion of 65–70% of the IdoA2S in a beef lung heparin. The products are stable and the oxirane could be isolated. The other 2-O-sulfated IdoA residues are unaltered, or appear as non-sulfated IdoA.

The second transformation described by Jaseja, M. et al., above, occurs when the oxirane is heated in alkaline solution. A product is produced that has a reduced IdoA-2-O-sulfate content, and a new uronic acid constituent appears which is isolatable. This second reaction was followed by $^{13}$C-nmr spectroscopy, and the disappearance of the resonances assigned to the oxirane carbons was accompanied by the appearance of new resonances distinct from IdoA. Resonances attributed to glucosamine residues were reportedly unaltered. This new residue was postulated to be α-L-galacturonic acid. This was later confirmed by detailed nmr analysis and chemical methods (Perlin, *Carbohydr. Res.* (1990) 200:437–447).

Rej and Perlin also reported (*Carbohydr. Res.* (1990) 200:437–447) that IdoA2S residues in heparin could be directly converted to the L-galacto isomer by heating an aqueous solution of heparin containing 0.1M sodium carbonate at 100°–110° C. The extent of this direct reaction was not well characterized, but typically yielded products with reduced anticoagulant activities (70 u/mg USP units) relative to the parent beef lung heparin (126 u/mg). The IdoA 2-O-sulfate residues were the only residues reported to be involved in this reaction. U.S. Pat. No. 5,104,860 claims similar products from reaction of alkaline heparin solutions at elevated temperatures having reduced anticoagulant and antithrombotic activities, useful for treating nephrolithiases. These compounds are characterized by the presence of a $^{13}$C-nmr resonance at 101.3 ppm, and optical rotation values between +15° and +40°, a reduced sulfate content (6–9% vs 10.6–11.6%), a sulfate:carboxylate ratio of about 1.2–1.7, and some free amine groups (0.4–2.1%). The relative content of native (IdoA2S) and transformed (L-GalA) residues was not provided for any of the products claimed.

The third transformation described by Jaseja, M. et al., above, of the oxirane containing heparin derivative, occurs when an alkaline solution (pH 12.5–12.8) of the epoxide is lyophilized. The products of this treatment were characterized by a reduced 2-O-sulfated IdoA content, and a corresponding increase in the amount of IdoA. It was also shown that treatment of native heparin under the same conditions yielded similar products, thus resulting in apparent direct 2-O desulfation. The products obtained from this third reaction sequence had variable extents of 2-O-desulfation. It is important to point out that one feature of the invention described below is the description of methods that permit controlling the amount of 2-O desulfation.

It is noteworthy that Perlin later reported (Perlin, *Carbohydr. Res.* (1992) 228:29–36.) a study using a model heparin compound, methyl 2-deoxy-2-sulfamino-a-D-glucopyranoside 3-O-sulfate, in which it was alkaline treated similar to heparin. The work was conducted to determine if the 3-O-sulfate groups from glucosamine residues of heparin would be lost during the alkaline lyophilization. The 3-O-sulfated compound was recovered unaltered from the reaction, leading to the conclusion that the 3-O-sulfate group in heparin is similarly unaffected.

It is further noteworthy that although Perlin describes heparin compositions that are 2-O desulfated, and methods to produce such compositions, he does not show a method to control the degree of 2-O, 3-O desulfation, nor does he show or suggest methods for producing compositions that can be variably desulfated including about 99% and 75%, or greater, desulfated at the 2-O and 3-O positions, respectively. Indeed, the work of both Jaseja, M. et al., above, and Perlin, above, suggest that only 2-O desulfation of heparin occurs under their reaction conditions, and moreover, that the extent of 2-O desulfation is highly variable.

U.S. Pat. No. 5,010,063 claims an epoxy heparin prepared by heating an alkaline solution of heparin. European patent application 483 733 claims an "epoxy heparide" formed from reaction of an over N-acetylated heparin in a sodium hydroxide solution, containing hydrogen peroxide, at elevated temperatures.

Non-Anticoagulant Heparin

There is a body of art that describes the production of non-anticoagulant heparin. Most of the publications describe non-anticoagulant heparin produced from depolymerized heparin/heparan sulfate, and separation of products by size. In a generally used procedure, the heparin starting material is depolymerized in the presence of nitrous acid with or without pretreatment to remove N-acetyl groups from any GlcNAc residues present. Nitrous acid, under the appropriate conditions, cleaves at the linkage between a GlcNS or GlcNH$_2$ residue and the uronic acid residue through which it is linked through a glucosamine α (1–4) uronic acid linkage. If the heparin has been deacetylated, all of the glucosamine→uronic acid residues are susceptible and complete depolymerization results in disaccharides. If the heparin has not been deacetylated, the glucosamine→uronic acid residues wherein the glucosamine is acetylated are resistant, and both disaccharides and tetrasaccharides and small amounts of higher oligosaccharides containing the resistant linkage result. In all cases, the glucosamine residue at the reducing terminus of the disaccharide or tetrasaccharide is convened to a 2,5-anhydromannose in the course of cleavage. This residue may further be reduced to the corresponding 2,5-anhydromannitol. These methods have been described by Bienkowski, M. J. and Conrad, H. E., *J Biol Chem* (1985) 260:356–365; Guo, Y. et at., *Anal Biochem* (1988) 168:54–62; and Guo, Y. and Conrad, H. E., Anal Biochem (1989) 176:96–104. These latter methods are useful in analyzing the structure of heparin and in assessing the results of various treatments of the heparin chains. Further, there have been considerable attempts to use the products of degradation of heparin from both complete and partial digestion with nitrous acid as described in the foregoing papers, or from heparinase digestion or from periodate oxidation followed by β-elimination. All of these processes can generate low molecular weight heparins for therapeutic use.

An example of non-anticoagulant depolymerized low molecular weight heparin is described in U.S. Pat. No. 4,990,502. It shows the treatment of heparin with periodate, followed by depolymerization with base, and reduction of the aldehydes generated in the periodate treatment. The resulting material is said to contain a mixture of polymers containing 17–33 residues and containing a multiplicity of residues of the formula

| IdoA-GlcAc | or | IdoA-GlcNS |
|---|---|---|
| 2S | | 2S | wherein the glucosamine residue is sulfated at the 3 and/or 6 position in an arbitrary manner, and wherein some of the IdoA residues may be replaced by cleaved IdoA or GlcA residues resulting from the periodate oxidation. These shortened polymeric chains are said to lack the binding site for ATIII but to be capable of inhibiting smooth muscle proliferation and to have physiological activities that include acceleration of tissue repair, prevention of atherogenous lesions, and prevention of the development of metastasis.

Treatment of heparin/heparan sulfate with periodate has also been reported by others. For instance, Fransson, L. A. and Lewis, W., *FEBS Lett* (1979) 97:119–123, describe a variety of conditions relating to the treatment of heparin/heparan sulfate with periodate and reduction by sodium borohydride or fragmentation in alkaline medium. Further, Fransson, L. A. et al., *Carbohydrate Res* (1980) 80:131–145, studied the chemistry of various forms of heparin produced with periodate. In one study, the treatment with periodate is followed by β-elimination in base to produce fragmentation. They further reported the treatment of heparin with periodate followed by partial acid hydrolysis which results in fragmentation of the chains and partial destruction of the functional groups.

Another example of a non-anticoagulant heparin is described by Casu, B. et al., *Arzneim Forsch/Drug Res* (1986) 36:637–642. They studied the effect of periodate oxidation on the anti-lipemic (lipoprotein lipase-releasing) activity of heparin. In this study, the heparin was oxidized with periodate and the products were reduced with borohydride. Although the authors stated that the product has the same molecular weight as the starting material, it is apparent from the figures presented in the paper that there is significant depolymerization.

PCT/SE92/00243 shows a non-anticoagulant heparin that has a molecular weight larger than the heparin starting material, and that is produced by periodate oxidation, partial depolymerization by alkali, and subsequent borohydride reduction.

Finally, the 2-O desulfated heparin compositions described by Jaseja, M. et al., in *Can. J. Chem.* (1989) 67:1449–1456, have non-anticoagulant activity.

It is important to note, that although non-anticoagulant heparins are known in the art, the art does not teach a method for producing non-anticoagulant heparins that can be about 99% and 75% or greater desulfated at the 2-O IdoA and 3-O GlcN positions, respectively.

Biological Properties of Non-Anticoagulant Heparins

Aside from their non-anticoagulant activity, NAC heparins have certain other novel biological properties. Some of these are described below.

Inhibition of Heparanase

The metastatic spread of tumor cells throughout the body is thought to be facilitated by enzymes secreted by tumor cells that degrade components of the basement membrane, thereby allowing tumor cells to disseminate via the circulation. One such enzyme is endo-β-D-glucuronidase, or heparanase, which degrades heparan sulfate glycosaminoglycans. Heparan sulfate is a prominent component of parenchymal cell basement membranes.

PCT patent application, WO 92/01003, shows that certain non-anticoagulant heparins act as heparanase inhibitors, and that they may be effective in lessening or preventing lung colonization by metastatic cell variants. The non-anticoagulant heparins were prepared from heparin by N-desulfation followed by N-acetylation, or N,O desulfation followed by N-desulfation. Hence, the non-anticoagulant heparins described in the above PCT application are distinct from the 2-O, 3-O desulfated heparin compositions of the instant invention.

Inhibition of Angiogenesis

Angiogenesis is the process whereby new blood vessels are produced. It is a process that may be associated with certain diseases, including arthritis, and the growth and metastasis of tumors. See, Mitchell and Wilks, *Annual Reports in Medicinal Chemistry* (Academic Press 1992) 27:139–148; Chapter 15.

Compounds that stimulate or inhibit angiogenesis can be identified using several assays known in the art. Perhaps the easiest assay to use is the chicken chorioallantoic membrane (CAM) assay. With this assay it has been shown that certain heparinoids inhibit angiogenesis when administered with certain angiostatic steroids. Folkman and Ingber, *Ann. Surg.* (1987) 206:374, Folkman et al., *Science* (1983) 221:719.

Inhibition of bFGF

Heparin or certain NAC heparins are known to bind bFGF with concomitant modulation of bFGFs mitogenic activity. The bFGF binding properties of certain heparins or heparin like molecules are described in this publication. For example, the results of a cell based competitive binding assay showed that there is little inhibition of binding of bFGF to a target cell by chemically modified heparin including completely desulfated, N-sulfated heparin, and N-desulfated, N-acetylated heparin.

Assays for measuring the effect of heparinoids on bFGF are known in the art. A cell based competitive binding assay is described by Ishihara, M. et al., *Anal Biochem* (1992) 202:310–315.

Platelet Inhibition

Heparin's best known property is its anti-coagulant activity, which is evidenced by the ability of heparin to prolong the bleeding time in animals. This occurs because heparin binds to the protease pro-inhibitor antithrombin III via its specific antithrombin III binding region. This, in turn, ultimately blocks the blood clotting cascade. Heparin is also known to have an anti-thrombotic effect, and at least in part this is a result of heparin's capacity to inhibit platelet aggregation. Interference with platelet aggregation causes a significant bleeding liability in some patients. Certain NAC heparins exhibit both non-anticoagulant activity and inhibit platelet aggregation. See, for example, co-owned U.S. Pat. No. 5,280,016, issued Jan. 18, 1994, or PCT Patent Application No. US92/02516, filed Mar. 27, 1992.

BRIEF DESCRIPTION OF THE INVENTION

In one aspect, the invention is directed to methods of O-desulfating heparin, preferably to produce 2-O, 3-O desulfated heparin compositions. The methods permit controlling the degree of 2-O, 3-O desulfation such that compositions can be produced that have a desired amount of desulfation including upto about 99% or 75% or greater desulfated at the 2-O and 3-O positions, respectively. The compositions have the following unique properties; anti-cancer activity, substantially no anticoagulant activity, inhibit platelet aggregation, reduced binding to bFGF relative to heparin, and heparanase and angiogenic inhibitory activity.

A second aspect of the invention is directed to substantially non-fragmented heparin compositions that can be 99% or 75% or greater desulfated at the 2-O and 3-O positions, respectively.

A third aspect of the invention is directed to 2-O, 3-O desulfated heparin fragments derived by chemical modification of heparin wherein the fragments can be 99% or 75% or greater desulfated at the 2-O and 3-O positions, respectively.

A fourth aspect of the invention is directed to methods of producing substantially unfermented 2-O, 3-O desulfated heparin compositions from heparin, wherein the compositions can be 99% or 75% or greater desulfated at the 2-O and 3-O positions, respectively, via an alkaline mediated chemical reaction having a bivalent cation in the reaction mixture.

A fifth aspect of the invention is a description of methods of making compositions of 2-O, 3-O desulfated heparin fragments from heparin, wherein the fragments can be 99% or 75% or greater desulfated at the 2-O and 3-O positions, respectively, via an alkaline mediated chemical reaction.

A sixth aspect of the invention is directed to methods of preventing or treating disease by administering to an animal host compositions of substantially unfragmented 2-O, 3-O desulfated heparin, or 2-O, 3-O desulfated heparin fragments wherein the compositions can be 99% or 75% or greater desulfated at the 2-O and 3-O positions, respectively.

A seventh aspect of the invention is the production of 2-O, 3-O desulfated heparin, or 2-O, 3-O desulfated heparin fragments having free amine groups that can be reacted with suitable reagents to yield N-modified 2-O, 3-O desulfated heparin analogues.

These and other aspects of the invention will be more fully understood upon a detailed consideration of the invention presented below.

MODES OF CARRYING OUT THE INVENTION

Figure 1:
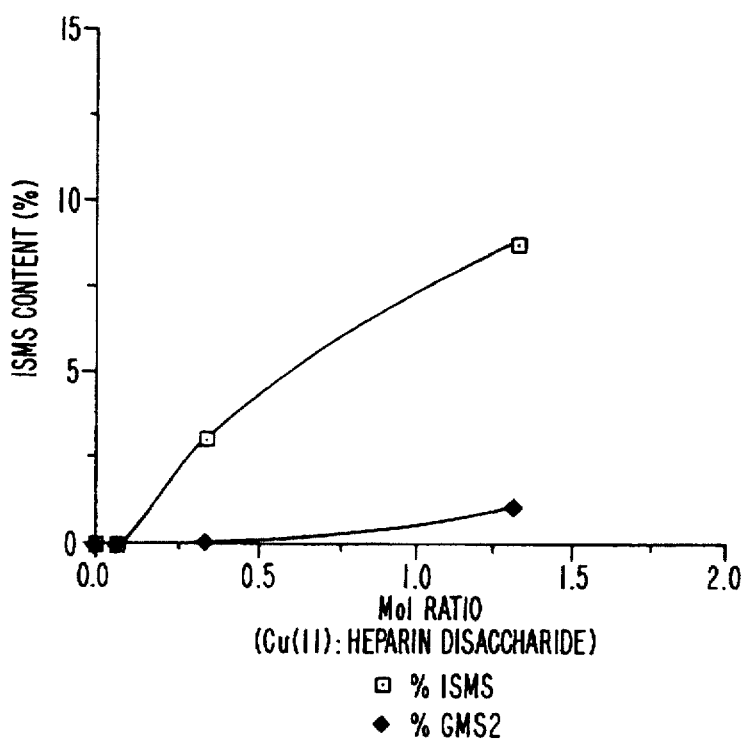
FIG. 1 shows the effect of copper II on the alkaline desulfation of heparin.

In its most general form, the instant invention relates to compositions and methods of producing the compositions, wherein the compositions consists of substantially unfragmented 2-O, 3-O desulfated heparin, or 2-O, 3-O desulfated heparin fragments. The methods permit controlling the per cent of 2-O, 3-O desulfation such that it can be about 99% or 75%, or greater, at these positions, respectively.

Throughout the specification reference is made to certain scientific publications, patents or patent applications. It is the intent of the applicants that these references be incorporated in their entirety into the application.

Understanding the invention will be facilitated by a brief discussion of certain of the technical terms used throughout the specification.

By "heparin/heparan sulfate" or "heparin" is meant a preparation obtained from tissues in a manner conventional for the preparation of heparin as an anticoagulant or otherwise synthesized and corresponding to that obtained from tissue. See Conrad, H. E., Heparin and Related Polysaccharides, Vol. 56, p. 18 of Annals of N.Y., Academy of Sc., Jun. 7, 1989, incorporated herein by reference. This preparation may include residues of D-glucuronic acid (GlcA), as characteristic of heparan sulfate as well as iduronic acid (IdoA) as characteristic of heparin. However, even though both GlcA and IdoA are present in both, they are present in different proportional amounts. The IdoA/GlcA ratio rises as heparan sulfate becomes more heparin-like. As described in the Background section above, the conversion of D-glucuronic acid to L-iduronic acid is a result of epimerization at the 5 carbon of GlcA residues in a heparan-type intermediate. This sequence of steps involved in such epimerization and conversion is understood in the art. To the extent that full conversion has not been made, heparan sulfate characteristics remain in the preparation. Because the precise nature of the polymeric chains in the preparations of heparin is not generally determined, and varies from preparation to preparation, the term "heparin/heparan sulfate" or "heparin" is intended to cover the range of mixtures encountered. Perhaps the main feature which distinguishes heparan sulfate from heparin is that the latter has anti-coagulant activity.

By heparin fragments, or low molecular weight heparin, is meant heparin that has been treated with any one of a number of reagents and methods that depolymerize heparin with a average molecular weight of 5–30 kd to compositions that have average molecular weights of 2–6.5 kd. Such reagents and methods are known in the art, and examples would include nitrous acid depolymerization, benzylation followed by alkaline depolymerization, peroxidative depolymerization, alkaline treatment, and enzymatic depolymerization with heparinase. See, Hirsh, J. and Levine, M., Blood (1992) 79:1–17.

The "heparin/heparan sulfate" or "heparin" preparation can be obtained from a variety of mammalian tissues, including, if desired, human tissue. Generally, porcine or bovine sources are used, and vascularized tissues are preferred. A preferred source of heparin starting material is porcine intestinal mucosa, and preparations labeled "heparin" prepared from this tissue source are commercially available. In general, the heparin starling material is prepared from the selected tissue source by allowing the tissue to undergo autolysis and extracting the tissue with alkali, followed by coagulation of the protein, and then precipitation of the heparin-protein complex from the supernatant by acidification. The complex is recovered by reprecipitation with a polar nonaqueous solvent, such as ethanol or acetone or their mixtures, and the fats are removed by extraction with an organic solvent such as ethanol and proteins by treatment with a proteolytic enzyme, such as trypsin. Suitable procedures for the preparation of the heparin starting material are found, for example, in Charles, A. F., et al., Biochem J (1936) 30: 1927–1933, and modifications of this basic procedure are also known, such as those disclosed by Coyne, E., in Chemistry and Biology of Heparin (1981 ) Elsevier Publishers, North Holland, N.Y., Lunblad, R. L. et al., eds.

"NAC-heparin" refers to a mixture of substantially non-anticoagulant, non-fragmented heparin obtained by subjecting commercially available heparin to one or more chemical treatments.

"Heparinoid" refers to glycosaminoglycans containing a 2-O-sulfated residue, including but not limited to heparin, chondroitin sulfates, dermatan sulfate, and NAC-heparin.

It is important to note that the disaccharide analysis of the compositions described and claimed herein are those presented by Guo and Conrad, Anal. Biochem. (1988) 168, 54–62. Such methods can detect 99% or greater loss of sulfate from the 2 position of IdoA. However, because of the low level of 3-O-sulfated GlcN residues present in hog mucosa heparin the methods do not allow reliable detection of 3-O desulfation greater than 75%.

In its general form the methods of the instant invention permit controlling the degree of 2-O, 3-O desulfation of unfragmented heparin, or heparin fragments, to yield compositions of substantially unfragmented 2-O, 3-O desulfated heparin, or 2-O, 3-O desulfated heparin fragments having a desired per cent of desulfation. The desulfation process can generally be performed using (a) methods involving lyophilization to accomplish the reaction, or (b) methods involving forming a paste of solid heparinoid with a base, preferably solid sodium or potassium hydroxide.

(a) This method consists of dissolving commercially available heparin, preferably Ming Han heparin, 170U/mg, or heparin fragments, also referred to as low molecular weight heparin (LMW heparin), in an aqueous alkaline solution (0.1–5.0% heparin or heparin fragments), in the presence of metal ions capable of regulating the extent of desulfation. Such ions include bivalent metal ions. The preferred ions are calcium and copper. Monovalent ions would also perform satisfactorily but would be used at higher concentrations than bivalent ions. Copper is the most preferred ion. Calcium and copper can be supplied in a variety of forms including $CaCl_2$, and $CuSO_4$. The ions are believed to interact with the 2-O and 3-O sulfate groups in a manner not yet fully understood to effectively shield them from desulfation. The degree of protection from desulfation is a function of ion concentration, which is elaborated more in the discussion below.

Hydroxide ion is present in the reaction; preferably in the form of an aqueous solution of an alkaline earth or alkali metal salt, to increase the pH to a level that initiates 2-O, 3-O desulfation of either heparin, or heparin fragments. One skilled in the art, using well known analytical techniques, including nuclear magnetic resonance (NMR) spectroscopy, will know to choose the preferred pH, reaction time, and other experimental parameters, by monitoring the loss of 2-O sulfate from iduronic acid. Similarly, the loss of 3-O sulfate from GlcN can be monitored as a function of reaction conditions, but as mentioned above, its loss cannot, however, be reliably quantitated greater than 75%. For example, the products can be identified using $^1$H- and $^{13}$C-nmr spectroscopy with detailed compositional characterization performed by HPLC analysis of nitrous acid generated disaccharides. Guo and Conrad, *Anal. Biochem.* (1988) 168:54–62; see also, Jaseja, M. et al., *Can. J. Chem.* (1989) 67:1449–1456. The reaction mixture is frozen, lyophilized to dryness, dissolved in water and excess hydroxide ion removed.

More specifically, heparin or heparin fragments, are dissolved in water to make a 0.1–5.0% solution. A variety of commercially available heparins may be used. The preferred heparin is Ming Han heparin, 170 U/mg. Depending on the degree of 2-O, 3-O desulfation desired a known amount of copper is added. A reducing agent (i.e. $NaBH_4$) may be added to prevent fragmentation of heparin. Indeed, because heparin is depolymerized at elevated pHs, a reducing agent is preferably added to maintain heparin in a substantially unfragmented form, preferably at pH's greater than 12.

Hydroxide ion is added to make the solution 0.05–1.0M with a preferred pH of 11–14. The preferred concentrations of hydroxide ion and heparin are 0.4M and 2%, respectively. Under these conditions, the 2-O, 3-O desulfated compositions are less than 10% depolymerized when compared to the heparin starting material. The solution is frozen and lyophilized to dryness. The residue is dissolved in water and excess hydroxide ion is removed, preferably using an ion-exchange resin (H+), or neutralization with acid. An aqueous solution of acetic or other mineral acids is preferred. The pH is raised to between 8–9 with sodium bicarbonate to form the sodium salt. After exhaustive dialysis or ultrafiltration, the solution is lyophilized to give substantially unfragmented 2-O, 3-O desulfated heparin (less than 10% of the starting material is depolymerized), or 2-O, 3-O desulfated heparin fragments. Alternately, the product can be precipitated from solution by the addition of ethanol using procedures well known in the art.

(b) This method consists of mixing commercially available heparin, preferably Ming Han heparin, 170 U/mg, or heparin fragments, also referred to as low molecular weight heparin (LMW heparin), with base, preferably solid sodium hydroxide (0.2–0.8 g NaOH/g of heparin or heparin fragments), in the presence of metal ions capable of regulating the extent of desulfation. Such ions include bivalent metal ions. The preferred ions are calcium and copper. Monovalent ions would also perform satisfactorily but would be used at higher concentrations than bivalent ions. Copper is the most preferred ion. Calcium and copper can be supplied in a variety of forms including $CaCl_2$, and $CuSO_4$. The ions are believed to interact with the 2-O and 3-O sulfate groups in a manner not yet fully understood to effectively shield them from desulfation. The degree of protection from desulfation is a function of ion concentration, which is elaborated more in the discussion below.

Hydroxide ion is present in the reaction, preferably in the form of a paste of an alkaline earth or alkali metal salt, to increase the pH to a level that initiates 2-O, 3-O desulfation of either heparin, or heparin fragments. One skilled in the art, using well known analytical techniques, including nuclear magnetic resonance (NMR) spectroscopy, will know to choose the preferred conditions, by monitoring the loss of 2-O sulfate from iduronic acid. Similarly, the loss of 3-O sulfate from GlcN can be monitored as a function of reaction conditions, as mentioned above. The reaction mixture is dissolved in water and excess hydroxide ion removed. The residue is purified to yield the product.

In some instances it might be beneficial to bleach the product to yield a white product.

More specifically, heparin or heparin fragments, and solid NaOH are mixed by grinding the solids together. Cold water is added to the cooled mixing vessel to form a homogenous paste. Depending on the degree of 2-O, 3-O desulfation desired a known amount of copper is added. A reducing agent, preferably $NaBH_4$, may be added to prevent fragmentation and to maintain heparin in a substantially undegraded form, preferably at pH's greater than 12.

0.2–0.8 g of hydroxide ion is added per gram of heparin. A small amount of cold water is added during the grinding process, and the grinding is continued in a vessel cooled at 0°–10° C. until a bright yellow homogenous paste is obtained. The paste is allowed to sit at room temperature for a period of time (15 min–6 h, preferably 3 h). The residue is dissolved in water and excess hydroxide ion is removed, preferably using an ion-exchange resin (H+), or neutralization with acid. An aqueous solution of acetic or other mineral acids is preferred. The pH is adjusted to between 6–8. After exhaustive dialysis or ultrafiltration, the solution is lyophilized to give substantially unfragmented 2-O, 3-O desulfated heparin (less than 10% of the starting material is depolymerized), or 2-O, 3-O desulfated heparin fragments. Alternately, the product can be precipitated from solution by the addition of ethanol using procedures well known in the art. The off-white product is optionally bleached to yield a final white solid product. Preferred bleaching conditions are those known in the art and are routinely used in heparin manufacturing process. The bleaching agents include, but are not limited to, potassium permanganate, peroxides and peracids.

The presence of bivalent metal ions in the reaction mixture causes desulfation to occur inversely proportional to the concentration of ions present, and the duration of the reaction. The products from this reaction are unique from other O-desulfated heparins in that only specific sulfate groups are lost, altering the gross sulfate content and charge of the product. It is important to note that this approach, and the data generated by it could be used to produce a standard curve that would allow a skilled practitioner of this art to select a particular bivalent ion concentration that would yield a heparin composition having a desired level of 2-O, 3-O desulfation. It will further be appreciated that such a standard curve could be produced by varying the heparin concentration.

A key aspect of the instant invention, which partially distinguishes it from the work of Jaseja, M. et al. *Can. J. Chem.* (1989) 67: 1449–1456, is the reaction conditions, particularly the hydroxide ion concentrations, that cause the loss of the 3-O-sulfate group from the glucosamine residues of heparin. It is important to be aware that since 3-O-sulfated glucosamine is present in the ATIII binding sequence of heparin, and is responsible for heparin's ATIII mediated anticoagulant activity; consequently its loss yields a non-anticoagulant composition.

Another key aspect of the reaction conditions employed is the appearance of free amine groups in the product (characterized by a resonance at 2.8 ppm in the $^1$H-nmr spectrum at a pH >9).The free amine residues arise from hydrolysis of a portion of the 2-acetamide groups. Typically, 0–5% of total glucosamine appears as a free amine. The free amines can be reacted using known reactions in order to convert them to sulfamino groups, acetamide groups, or other N-acyl groups. Thus, the instant invention also encompasses N-modified heparin analogues.

N-modified heparins have been prepared from partially or completely N-deacetylated heparin (Y. Guo and H. E. Conrad, *Anal. Biochem.*, (1989) 176:96–104; and Shaklee and Conrad *Biochem J.* (984) 217:187–197), followed by: (a) N-sulfation with appropriate N-sulfation reagents (L. Ayotte and A. S. Perlin, *Carbohydr. Res.* (1986) 145:267–277) to give analogues higher in sulfamino content and thus more anionic, (b) N-acylation with anhydrides ($R(CO)_2O$, where $R=\!\!-\!\!(CH_2)_nH$ and aryl) to yield analogues having hydrophobic substituents that may enhance in binding to bioactive proteins by hydrophobic interaction. Additional compositions can also be produced by altering the sequence of these reactions, such that the 2-O, 3-O desulfated heparin compositions of the invention are subjected to N-deacetylation conditions, followed by re-N sulfation or acylation by procedures known in the art.

Additional N-modified analogues can be prepared by partial or complete N-desulfation of heparin (L. Ayotte and A. S. Perlin, *Carbohydr. Res.* (1986) 145: 267–277) using known procedures, followed by re-N-acylation with anhydrides ($R(CO)_2O$, where $R=\!\!-\!\!(CH_2)_nH$ and aryl) to yield heparin compositions with reduced anionic charge. These compositions can also be prepared from the 2-O, 3-O desulfated heparin compositions of the invention by N-desulfating the product and then re-N-acylating to yield the appropriate product analogue.

Labeled Forms of the Invention Non-Anticoagulant Compositions

The compositions of the invention can be provided with fluorescent, radioisotope, or enzyme labels as desired. Conventional techniques for coupling of label to carbohydrates or related moieties can be used. Such techniques are well established in the art. See, for example, U.S. Pat. No. 4,613,665. The labeled mixtures of the invention may be used to identify sites of disease as well as in competitive immunoassays, and as a means to trace the pharmacokinetics of the compositions in vivo. Suitable radioisotope labels for this purpose include hydrogen[3], iodine[131], indium[111], technetium[99], and phosphorus[32]. Suitable enzymic labels include alkaline phosphatase, glucose-6-phosphate-dehydrogenase, and horseradish peroxidase. Particularly preferred fluorescent labels include fluorescein and dansyl. A wide variety of labels of all three types is known in the art.

Administration and Use

The non-anticoagulant heparin compositions of the instant invention are useful in therapeutic applications for treating or preventing a variety of diseases including cancer, inflammation, and diseases caused or exacerbated by platelet aggregation, heparanase or angiogenic activity. The instant 2-O, 3-O desulfated heparin compositions, because of their anti-angiogenic activity, will be preferably applied for the beneficial treatment of angiogenic based diseases. One such class of diseases is retinopathies. A member of this class is diabetic retinopathy that will be favorably treated by the compositions of the instant invention.

It should be noted that the preferred therapeutic composition consists of 2-O, 3-O desulfated heparin fragments. Because of their reduced size such fragments exhibit favored bioavailability and pharmacokinetic properties. See, Hirsh, J. and Levine, M., *Blood* (1992) 79:1–17.

Administration of either substantially unfragmented 2-O, 3-O desulfated heparin, or 2-O, 3-O desulfated heparin fragments is typically by routes appropriate for glycosaminoglycan compositions, and generally includes systemic administration, such as by injection.

Particularly preferred is intravenous injection, as continuous injection over long time periods can be easily continued. Also preferred are introduction into the vascular system through intraluminal administration or by adventitial administration using osmotic pumps or implants. Typical implants contain biodegradable materials such as collagen, polylactate, polylactate/polyglycoside mixtures, and the like. These may be formulated as patches or beads. Typical dosage ranges are in the range of 0.1–10 mg/kg/hr on a constant basis over a period of 5–30, preferably 7–14, days. Particularly preferred dosage is about 0.3 mg/kg/hr, or, for a 70 kg adult, 21 mg/hr or about 500 mg/day.

Other modes of administration are less preferred but may be more convenient. Injection subcutaneously at a lower dose or administered orally at a slightly higher dose than intravenous injection, or by transmembrane or transdermal or other topical administration for localized injury may also be effective. Localized administration through a continuous release device, such as a supporting matrix, perhaps included in a vascular graft material, is particularly useful where the location of the trauma is accessible.

Formulations suitable for the foregoing modes of administration are known in the art, and a suitable compendium of formulations is found in *Remington's Pharmaceutical Sciences*, Mack Publishing Company, Easton, Pa., latest edition.

The compositions of the invention may also be labeled using typical methods such as radiolabeling, fluorescent labeling, chromophores or enzymes, and used to assay the amount of such compositions in a biological sample following its administration. Suitable protocols for competitive assays of analytes in biological samples are well known in the art, and generally involve treatment of the sample, in admixture with the labeled competitor, with a specific binding partner which is reactive with the analyte such as, typically, an immunoglobulin or fragment thereof. The antibodies prepared according to the invention, as described below, are useful for this purpose. The binding of analyte and competitor to the antibody can be measured by removing the bound complex and assaying either the complex or the supernatant for the label. The separation can be made more facile by preliminary conjugation of the specific binding partner to a solid support. Such techniques are well known in the art, and the protocols available for such competitive assays are too numerous and too well known to be set forth in detail here.

Antibodies may be prepared to 2-O, 3-O desulfated heparin, or 2-O, 3-O desulfated heparin fragments by direct injection into an appropriate animal host, or by coupling the compositions to suitable carders and administering the coupled materials to mammalian or other vertebrate subjects in standard immunization protocols with proper inclusion of adjuvants. Suitable immunogeuic carriers include, for example, Keyhole Limpet Hemocyanin (KLH), tetanus toxoid, various serum albumins such as bovine serum albumin (BSA) and certain viral proteins such as rotaviral VP6 protein. These coupled materials are then administered in repeated injections to subjects such as rabbits, rats or mice and antibody titers monitored by standard immunoassays techniques. The resulting antisera may be used per se or the antibody-secreting cells generated by the immunization may be immortalized using standard techniques and used as a source of monoclonal preparations which are immunoreactive with 2-O, 3-O desulfated heparin, or 2-O, 3-O desulfated heparin fragments.

Methods to conjugate 2-O, 3-O desulfated heparin, or 2-O, 3-O desulfated heparin fragments to carders are known in the art. The compositions may be linked to the carrier by, for example, homo- or heterobifunctional linkers such as those marketed by Pierce Chemical Company, Rockford, Ill. Certain covalent linkers are described in U.S. Pat. No. 4,954,637.

Murine or human monoclonal preparations can be obtained by in vivo or in vitro immortalization of peripheral blood lymphocytes or spleen cells of animals using methods well known in the art, such as fusion with immortalizing cells as described by Kohler and Millstein *Nature* (1975) 256:495; and Fendly, et al., *Hybridoma* (1987) 6:359. In vitro techniques are generally described by Luben, R. and Mohler, M., *Molecular Immunology* (1980) 17:635; Reading, C. *Methods in Enzymology* (1986) 121:18 (Part 1); or Voss, B., *Methods in Enzymology* (1986) 121:27. Recombinant and/or humanized antibody may also be generated using methods known in the art.

Properties of 2-O, 3-O Desulfated Heparin or 2-O, 3-O Desulfated Heparin Fragments As discussed above, heparin and non-anticoagulant heparins are biologically active. Certain assays were conducted to determine the biological properties of the instant invention compositions, and compare these to the properties of heparin or non-anticoagulant heparins. A particularly noteworthy property of the 2-O, 3-O desulfated heparin is its low in vivo toxicity. The properties studied and the assays used are described in detail in the Examples below.

The following examples are intended to illustrate but not to limit the invention. For example, those skilled in the art would know that there are materials and methods that can be substituted for those described below, and still come within the scope of what is taught in the Examples.

EXAMPLE 1

Production of 2-O, 3-O Desulfated Heparin 1.0 g of Ming Han hog mucosal heparin was dissolved in 180 ml of water and 20 ml of 1M NaOH was added to make the solution 0.1M in NaOH, and 0.5% in heparin. The solution was frozen and lyophilized to dryness. The resulting crusty yellow colored residue was dissolved in 50 ml of water and then adjusted to pH 6–7 by the addition of 20% acetic acid solution. Solid sodium bicarbonate was added to bring the pH up to 8–9. The solution was exhaustively dialyzed and lyophilized thereby yielding 0.73 g of solid product.

The product was subjected to various assays, including a determination of APTT values, and disaccharide analysis. These assays were also used in the following Examples, below. The values presented are relative to the heparin starling material. A commercial kit obtained from Baxter laboratories was used to determine APTT values. The manufacture's instructions regarding the use of the kit were followed. The values are expressed as the % APTT relative to heparin.

The 2-O, 3-O desulfated heparin composition of the invention was characterized using $^1$H- and $^{13}$C-nmr spectroscopy with detailed compositional characterization performed by HPLC analysis of nitrous acid generated disaccharides, as described by Guo, Y. and Conrad, H. E. *Analyt Biochem* (1989) 176:96–104. Each sample was treated with 70% hydrazine and nitrous acid at pHs 1.5 and 4.0, and the resulting disaccharides were quantified using the reversed phase ion pairing HPLC method described by Guo and Conrad, Anal. Biochem. (1988) 168, 54–62.

Using these assays the product isolated as described above exhibited the following % anticoagulant activity (APTT), IdoA 2-S, and $GMS_2$, respectively; 10.0, 1.1, and <1.

EXAMPLE 2

Production of 2-O, 3-O Desulfated Heparin

Ming Han hog mucosal heparin (5 g) and solid NaOH (4 g) were mixed by grinding the solids together in a vessel cooled at 0°–10° C. until a bright yellow homogenous paste is obtained. A reducing agent ($NaBH_4$, 1 g) was added to limit alkaline induced degradation of the heparinoid and the product. A small amount of water (3 ml) was added during the grinding process, and the mixing was continued until a bright yellow homogenous paste was obtained. The paste was allowed to sit at room temperature for 3 h. Water was added to dissolve the paste, and the solution was immediately neutralized to pH 7 by the addition of 20% acetic acid solution. The product was purified by ultrafiltration (MWCO 1000 Da), and lyophilized to yield the final off-white product.

These compositions are essentially identical to the compositions prepared by the lyophilization method described in Example 1, as determined by disaccharide analysis, $[MW]_w$, APTT and $^1$H-NMR.

EXAMPLE 3

Effect of Calcium on the Production of 2-O, 3-O Desulfated Heparin 1.0 g of Ming Han hog mucosal heparin was dissolved in 100 ml distilled water, to which was added 250 mg of $CaCl_2$. This solution was mixed with 100 ml of 0.2M sodium hydroxide solution, frozen and lyophilized to dryness. The resulting crusty yellow colored residue was dissolved in 50 ml of water and then adjusted to pH 6–7 by the addition of 20% acetic acid solution. Solid sodium bicarbonate was then added to bring the pH up to 8–9. The solution was then exhaustively dialyzed and after lyophilization was isolated as a solid product (0.76 g). The % anticoagulant activity, IdoA 2-S, and $GMS_2$ were, respectively; 5.5, 3.3, and 1.9.

EXAMPLE 4

Effect of High Hydroxide Concentration on 2-O, 3-O Desulfation

Heparin (20.0 g, Ming Han hog mucosal was dissolved in 1000 ml of 0.4M sodium hydroxide solution, frozen and lyophilized to dryness. The resulting crusty yellow colored residue was dissolved in 250 ml of water and adjusted to pH 6-7 by the addition of 20% acetic acid solution. Solid sodium bicarbonate was added to bring the pH up to 8-9. The solution was then exhaustively dialyzed and after lyophilization was isolated as a solid product (12.0 g). The % anticoagulant activity, IS, and GMS2 were, respectively; 8.0, <1.0, and <1.0.

EXAMPLE 5

Effect of Copper on the Production of 2-O, 3-O Desulfated Heparin

Experiments were conducted to show that the amount of 2-O, 3-O desulfated heparin produced under the alkaline conditions of Example 1 could be controlled by including copper in the reaction mixture. The materials and methods used in Example 3 were used here with the exception that copper II was substituted for 0.1M calcium, and the ratio of copper II to heparin disaccharide was varied.

FIG. 1 shows the per cent of residual ISMS and 3-O-sulfated GlcN (GMS2) remaining at the end of the reaction as a function of the copper II/heparin disaccharide mole ratio. It is apparent from FIG. 1 that the per cent of ISMS remaining correlates with the concentration of copper present in the reaction mixture. A similar relationship is seen for GMS2.

Figure 2:
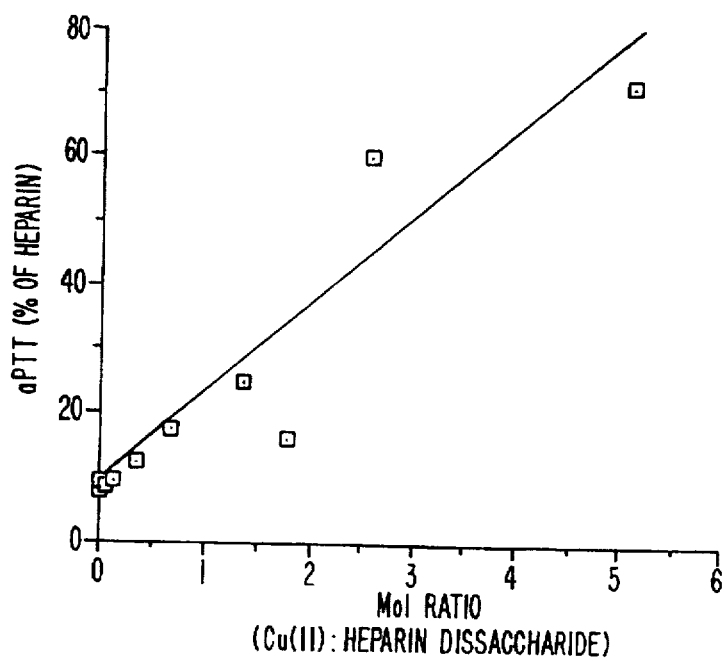
FIG. 2 shows the % APTT activity and % residual IS remaining of 2-O desulfated heparin compositions of the instant invention as a function of the ratio of copper to iduronic acid (2S) in the reaction mixture. The Cu (II) concentration is given in mmoles.

FIG. 2 shows the % APTT activity remaining at the concentrations of copper II tested: as the ratio of copper II to heparin disaccharide increases the % APTT increases. Thus, it is concluded that copper II protects against 2-O, 3-O desulfation. It is important to note that these data could be used as a standard curve that would allow a skilled practitioner of this art to select a particular copper II concentration that would yield a heparin composition having a desired level of 2-O, 3-O desulfation.

EXAMPLE 6

Effect of Permanganate Bleaching on 2-O, 3-O Desulfated Heparin

Some depolymerization can occur when heparin is lyophilized from alkaline solution to yield 2-O, 3-O-desulfated heparin or fractions and fragments thereof. The extent of depolymerization is related to the amount of excess base present during the lyophilization reaction, as well as to the temperature reached during dissolution of the lyophilized product and to the time in the alkaline solution prior to neutralization. It is believed that depolymerization occurs by β-elimination reaction leading to a Δ-4,5-unsaturated uronic acid non-reducing terminal residue. This is supported by the appearance of a resonance (5.8 ppm) in the $^1$H-NMR spectrum of the product that is characteristic of the Δ-4,5-unsaturated uronic acid residue formed by β-elimination of heparin. The greater the extent of depolymerization observed, the greater the relative intensity of this resonance at 5.8 ppm.

The 2-O, 3-O-desulfated heparin prepared according to the process described in Example 1 was treated with 8% KMnO$_4$ solution at neutral pH for 30-60 minutes at 50° C. The reaction was worked up under standard heparin manufacturing conditions to yield the bleached product. The permanganate bleaching of 2-O, 3-O-desulfated heparin results in a modification causing the loss of the Δ4,5 unsaturated residue. The disaccharide composition and other characterization data for the 2-O, 3-O-desulfated heparin products are not substantially changed by this bleaching step.

EXAMPLE 7

Production of 2-O, 3-O Desulfated Heparin Fragments 1.0 g of low molecular weight (5 kd) hog mucosal heparin, obtained from Celsus Laboratories, was dissolved in 200 ml of 0.1M sodium hydroxide solution. The solution was frozen and lyophilized to dryness, yielding a crusty yellow colored residue. The residue was dissolved in 50 ml of water and the solution adjusted to pH 6-7 by the addition of 20% acetic acid solution. Solid sodium bicarbonate was then added to bring the pH up to 8-9. The solution was exhaustively dialyzed and after lyophilization was isolated as a solid product (0.77 g). The % anticoagulant activity was 1.2. IdoA 2-S and GMS$_2$ were not detectable, indicating that the heparin starting material is >99% desulfated.

EXAMPLE 8

Production of 2-O, 3-O Desulfated Heparin Fragments 5.0 g of low molecular weight (5 kd) hog mucosal heparin, obtained from Celsus Laboratories and solid NaOH (4 g) were mixed by grinding the solids together in a vessel cooled at 0°-10° C. until a bright yellow homogenous paste is obtained. A reducing agent (NaBH$_4$, 1 g) was added to limit alkaline induced degradation of the heparinoid and the product. A small amount of water (3 ml) was added during the grinding process, and the grinding was continued until a bright yellow homogenous paste was obtained. The paste was allowed to sit at room temperature for 3 h. Water was added to dissolve the paste, and the solution was immediately neutralized to pH 7 by the addition of 20% acetic acid solution. The product was purified by ultrafiltration (MWCO 1000Da), and lyophilized to yield the final off-white product.

These compositions are essentially identical to the compositions prepared by the lyophilization method described in Example 7, as determined by disaccharide analysis, [MW]$_w$, APTT and 1H-NMR.

EXAMPLE 9

Effect of Limiting Hydroxide Ion Concentration on 2-O, 3-O Desulfation of Heparin Fragments 1.0 g of low molecular weight (5 Kd) hog mucosal heparin, obtained from Celsus Laboratories, was dissolved in 200 ml of 0.05M sodium hydroxide solution. This molarity is one half that used in the preceding example. The solution was frozen and lyophilized to dryness, yielding a crusty yellow colored residue. The residue was dissolved in 50 ml of water and the solution adjusted to pH 6-7 by the addition of 20% acetic acid solution. Solid sodium bicarbonate was then added to bring the pH up to 8-9. The solution was exhaustively dialyzed and after lyophilization was isolated as a solid product (0.77 g). The % anticoagulant activity, IdoA 2-S, and GMS2 were, respectively; 23, 12.1, and 3.8.

EXAMPLE 10

Production of 2-O, 3-O Desulfated Heparin From Re-N-Sulfated N-Deacetylated Heparin 1.0 g of re-N-sulfated N-deacetylated heparin produced as described by Lloyd, A. G. et. al., *Biochem. Pharmacol* (1971) 20:637-648 and Guo, Y. and Conrad, H. E., *Anal Biochem* (1989) 176:96-104 was dissolved in 200 ml of 0.1M sodium hydroxide solution, frozen and lyophilized to dryness. The resulting crusty yellow colored residue was dissolved in 50 ml of water and adjusted to pH 6-7 by the addition of a 20% acetic acid solution. Solid sodium bicarbonate was added to bring the pH up to 8–9, and the solution was exhaustively dialyzed and lyophilized, yielding 0.73 g of a solid product.

The % anticoagulant activity, IdoA 2-S, and GMS2 were, respectively; 9.5, 1.2, and <1.0.

EXAMPLE 11

Anti-Angiogenic Activity

Compounds that stimulate or inhibit angiogenesis can be identified using several assays known in the art. The heparinoids of the instant invention were tested using the chicken chorioallantoic membrane (CAM) assay. The assay was performed as described by Castellot et. al., *J. of Cellular Physiology* (1986) 127:323–329, with the exception that samples were evaluated for their efficacy to inhibit neovascularization. Agarose pellets containing 50 μg of hydrocortisone, or hydrocortisone plus different amounts of 2-O, 3-O desulfated heparin were incubated on the CAM for 3–4 days before scoring the results. 2-O, 3-O desulfated heparin was produced as described in Example 1.

Table 1 shows the results. It is apparent that the 2-O, 3-O desulfated heparin composition exhibits angiostatic activity. Angiostatic activity is defined as a partial clearing or an avascular zone around the pellet. In all cases, pellets at each heparinoid concentration contained 50 μg of hydrocortisone.

The number in parenthesis in the Table is the percent of the total embryos scored that exhibited no effect, a partial clearing, or an avascular zone. For example, 3.125 μg/ml of the 2-O, 3-O desulfated heparin had no effect on 20 embryos and a partial clearing on 4 embryos. Thus, under these conditions 83.3% of the embryos showed no effect and 16.7% exhibited a partial clearing.

TABLE 1

Chick Chorioallantoic Membrane Bioassay
Compound 2-O, 3-O Desulfated Heparin

| Composition (μg/ml) Non-anticoagulant heparin | No Effect (0) | Partial Clearing (+) | Avascular Zone (++) |
|---|---|---|---|
| 0.00 | 22 (100.0) | | |
| 3.125 | 20 (83.3) | 4 (16.7) | |
| 6.25 | 16 (59.3) | 9 (33.3) | 2 (7.4) |
| 12.5 | 9 (36.0) | 10 (40.0) | 6 (24.0) |
| 25.0 | 14 (58.3) | 10 (41.7) | |
| 50.0 | 12 (41.4) | 13 (44.8) | 4 (13.8) |

EXAMPLE 12

Heparanase Inhibitory Activities of 2-O, 3-O and 2-O Desulfated Heparin Compositions The 2-O, 3-O desulfated heparin composition of the instant invention was tested for heparanase inhibitory activity using heparanase from a rat hepatoma cell line. The cell line is described by Gerschenson, et al., *Science* (1970) 170:859–861. Further, its inhibitory activity was compared to 2-O desulfated heparin of Jaseja, M. et al., *Can. J. Chem.* (1989) 67:1449–1456. Recall that this composition is produced from beef lung heparin, unlike the instant compositions which are produced from hog mucosal heparin. 2-O, 3-O desulfated heparin was produced as described in Example 1, and the 2-O desulfated heparin composition was supplied by Dr. Perlin, a co-author of the Jaseja, M. et al publication, above.

The procedures for isolating heparanase from hepatoma cells, and the methods for assaying the activity of the enzyme are known by those skilled in the art. The following procedures and materials were used.

Confluent rat hepatoma cell cultures were grown in standard cell culture flask, and washed 3 times with 10 ml of a 50 mM Hepes solution containing 0.25M sucrose and 0.14 M NaCl, pH 7.4. Next, 1 ml of a 50 mM MES buffer pH 5.2, containing 0.14M NaCl, 6 mM sodium azide, and certain protease inhibitors was added and the cells removed from the flask using a disposable cell scraper. The following protease inhibitors were present in the MES buffer: 0.2 μg/ml aprotinin, 0.5 μg/ml leupeptin, 100 μg/ml soybean trypsin inhibitor, 1 mM PMSF, 2 mM EDTA (sodium salt), and 15 mM D-saccharic acid 1,4 lactone (exoglucuronidase inhibitor).

The cells were added to a 7 ml Dounce homogenizer, freezed/thawed 3 times in an ethanol/dry ice bath, and homogenized with 15 strokes using a tight pestle. The resulting cell lysates were placed in a 2 ml centrifuge tube and centrifuged at 4° C. for 30 minutes at 16,000×g. The supernatant was removed, and the protein concentration in the supernatant determined using the Macro BCA protein assay. BSA was used as a standard.

Heparanase activity was quantified by measuring soluble N-$^3$H-acetylated pancreas heparan sulfate fragments derived from uncleaved N-$^3$H-acetylated pancreas heparan sulfate by cetylpyridinium chloride (CPC) precipitation. N-$^3$H-acetylated pancreas heparan sulfate had a weight average molecular weight, or Mw, of about 12,000. The following procedures were used.

Rat hepatoma cell supernatant, isolated as described above, containing 10 μg of protein was brought up to 30 μl with 50 mM MES buffer pH 5.2 containing 0.14M NaCl, 6 mM sodium azide and the protease inhibitors described above, and added to siliconized 1.5 ml microcentrifuge tubes. Next, $^3$H-acetylated pancreas heparan sulfate (93 ng, 30,000 cpm) in 10 μl of 200 mM MES buffer pH 5.2 containing 0.14M NaCl was added to tubes containing the rat hepatoma cell supernatant. 10 μl of distilled water containing various concentrations of 2-O, 3-O desulfated heparin, or 2-O desulfated heparin of Jaseja, M., et al., above, was added. The assay was run in triplicate for each inhibitor concentration. Three "0" time points were run as controls in which no inhibitor was added. It was previously shown that the highest concentration of inhibitor does not affect precipitation of the intact radiolabeled heparan sulfate substrate.

The enzyme substrate inhibitor mixture was spun in a microcentrifuge, after which the tubes were incubated at 37° C. for 30 minutes. The "0" time points were maintained on ice. After the appropriate time, the reaction was stopped by adding to the reaction tubes the following:

1) 150 μl of an aqueous heparin solution (0.33 mg/ml)
2) 200 μl of 100 mM sodium acetate pH 5.5
3) 100 μl of CPC (0.6% in water)

Next, the tubes were vortexed, incubated for 60 minutes at room temperature, and then centrifuged for 10 minutes at 4,000×g in a 5415C Eppendoff centrifuge. The supernatant was removed and assayed for $^3$H by liquid scintillation counting.

Figure 3:
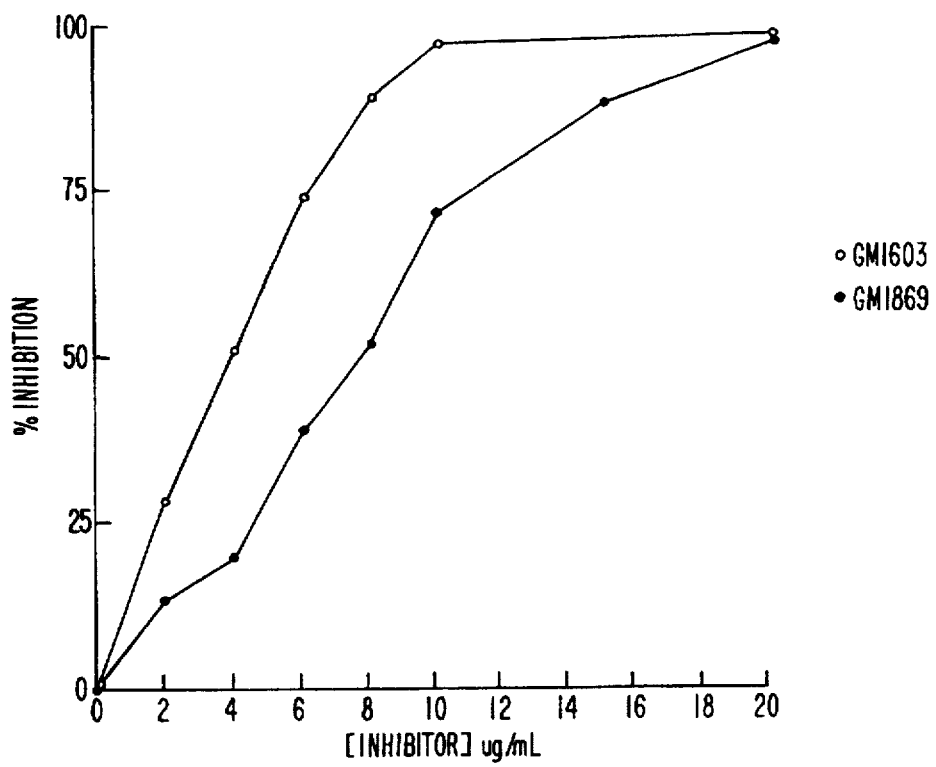
FIG. 3 compares the heparanase inhibitory activity of 2-O, 3-O desulfated heparin produced by the methods of the instant invention, and, 2-O desulfated heparin produced by the methods of Jaseja, M., et al., Can. J. Chem. (1989) 67:1449–1456.

FIG. 3 shows the results. The 2-O, 3-O desulfated heparin composition of the instant invention is denoted GM 1603 while the 2-O desulfated composition of Jaseja, M., et al., is denoted GM1869. It is apparent that the 2-O, 3-O desulfated heparin composition is significantly more active than the 2-O desulfated composition. Indeed, the $IC_{50}$ values were 4.0 μg/ml and 7.6 μg/ml, respectively.

Thus, these results establish that the 2-O, 3-O desulfated heparin composition of the instant invention is a heparanase inhibitor, and further, it is significantly more active than the 2-O desulfated heparin composition of Jaseja, M. et al.

EXAMPLE 13

Activity of 2-O, 3-O Desulfated Heparin in bFGF Binding Assay

A cell based assay as described by Ishihara, M. et al., *Analytical Biochemistry* (1992) 202:310–315 was used to measure the effect of 2-O, 3-O desulfated heparin on bFGF binding. 2-O, 3-O desulfated heparin was produced as described in Example 1. Similar experiments were run using Ming Han hog mucosal heparin and the non-anticoagulant heparin composition produced as described in U.S. Pat. No. 5,280,016, or PCT Patent Application No. US92/02516, filed Mar. 27, 1992. This composition consists of heparin oxidized with sodium periodate and subsequent reduction with sodium borohydride.

The assay is based on the observation that bFGF binds to a lymphoblastoid cell line, RO-12, that expresses hamster syndecan, and that this interaction can be inhibited by compounds that bind to bFGF. The cell line is transfected with cDNA that encodes the core protein of syndecan. Hamster syndecan is known to bind bFGF, presumably because heparan sulfate chains are bound to the core protein by the RO-12 cell line.

The assay was run as follows. Fifty microliters of 10 µg/ml human recombinant bFGF was added to wells of a 96-well tissue culture plate and incubated overnight at 4° C. The wells were aspirated with PBS to remove any unbound bFGF, rinsed twice with PBS, and subsequently incubated with PBS containing 5% (v/v) fetal bovine serum for 1 hour at room temperature. RO-12 cells were suspended at a density of 3×10$^6$ cells/ml in PBS containing 5% fetal bovine serum. To this mixture was added the desired amount of 2-O, 3-O desulfated heparin, or heparin. The compositions were used, in µg/ml, at concentrations of 50, 25, 12.5, 6.3, 3.1, 1.6, and 0.8. They were made up in PBS plus 2.5% fetal bovine serum. A control was also run, containing only PBS plus 2.5% fetal bovine serum. Next, 100 µl of the cell mixture was immediately added to the microtiter wells, and incubated for 5 minutes, after which the wells were washed 3 times with PBS. Finally, the amount of cell protein bound to the wells was determined by dissolving the cell pellets in 20 µl of 5% SDS and measuring the protein concentration of the cell lysates. BSA was used as the standard.

The results established that the concentrations of 2-O, 3-O desulfated heparin, the non-anticoagulant heparin composition produced as described in U.S. Pat. No. 5,280,016, or heparin that inhibits 50% of cell binding to bFGF were >50 µg/ml, <1 µg/ml and <1 µg/ml, respectively. Thus, 2-O, 3-O desulfated heparin composition of the instant invention has greatly reduced binding activity to bFGF relative to heparin, or the non-anticoagulant heparin composition described in U.S. Pat. No. 5,280,016.

EXAMPLE 14

Effect of 2-O, 3-O Desulfated Heparin on Ristocetin Induced Platelet Aggregation The effect of 2-O, 3-O desulfated heparin on ristocetin induced platelet aggregation was measured in the presence of vWF as described by Sobel et al., *J. Clin. Invest.* (1992) 87:1787–1793, and Kelton et al., *Thromb Res* (1980) 18:477–483. Also tested were the effects of Ming Han hog mucosal heparin, and the NAC heparin described in U.S. Pat. No. 5,280,016, or PCT Patent Application No. US92/02516, filed Mar. 27, 1992. 2-O, 3-O desulfated heparin was produced as described in Example 1.

The experiment was conducted as follows. Platelet-rich plasma was prepared from citrated whole blood of 300–500 gram male guinea-pigs by low speed centrifugation to sediment the red blood cells. The guinea pigs were anesthetized with methoxyflurane. The upper layer was harvested and used to determine the effects of the heparinoids on platelet aggregation. The remaining red blood cell rich plasma was centrifuged at high speed in order to prepare a platelet poor plasma fraction that was used as a blank in the aggregometer.

400 µl samples, consisting of 200 µl of platelet-rich plasma and 200 µl of platelet poor plasma, were placed in the light path of a dual aggregation module (Payton) two-channel aggregometer, and preincubated at 37° C. with various concentrations of heparinoid test material or PBS buffer control for 10 minutes. The samples were continuously stirred at 1,000 rpm. Aggregation was induced by adding 6 µl of ristocetin (stock solution, 125 mg/ml in 0.9% sterile saline) and aggregation recorded as the change in light transmission using the platelet poor plasma as a blank.

2-O, 3-O desulfated heparin and heparin were tested at various concentrations, the highest being 1000 µg/ml, and the remaining being 2 fold serial dilutions.

The results were expressed as the EC$_{70}$ concentrations, or the concentration that was effective at inhibiting 70% aggregation. The EC$_{70}$ concentrations for 2-O, 3-O desulfated heparin and for the NAC heparin described in U.S. Pat. No. 5,280,016, were expressed relative to heparin which was taken as 1. The EC$_{70}$ concentrations for 2-O, 3-O desulfated heparin and for the NAC heparin shown in the patent application were 0.4 and 2-4, respectively.

Thus, the 2-O, 3-O desulfated heparin composition of the instant invention inhibits platelet aggregation to a lesser extent than heparin indicating possibly reduced bleeding potential.

EXAMPLE 15

Toxicity of 2-O, 3-O Desulfated Heparin Compositions

Experiments were done to determine the in vivo toxicity of the 2-O, 3-O desulfated heparin compositions. A group of three (3) mice was administered 2-O, 3-O desulfated heparin subcutaneously, once a day according to the following schedule: 20 mg/kg on day 1, 40 mg/kg on day 2, 80 mg/kg on day 3, and 160 mg/kg on day 4. At the end of day 4, two (2) of the mice showed no signs of toxicity while the third, although healthy, presented subcutaneous swelling at the site of injection. Based on these results, and considering the high doses used, there is little or no in vivo toxicity associated with the 2-O, 3-O desulfated heparin compositions.

EXAMPLE 16

Effect of 2-O, 3-O Desulfated Heparin Compositions on Tumor Growth

Experiments were conducted to test the efficacy of 2-O, 3-O desulfated heparin compositions on tumor growth in an animal model system, the nude mouse, that closely mimics the human condition. Two human tumor cell lines were utilized; a pancreatic adenocarcinoma, CAPAN-2, and a mammary adenocarcinoma, MDA231. Both cell lines grow aggressively in nude mice, and CAPAN-2 exhibits the multiple drug resistant phenotype.

The experiments were conducted as follows: male, 20 gram, nude mice, in groups of ten, were inoculated subcutaneously with $3\times10^6$ viable CAPAN-2 cells in 0.2 ml PBS/matrigel (1:3). Twenty four hours latter, the mice were subcutaneously injected with 2-O, 3-O desulfated heparin at a dose of 60 mg/kg, made up in PBS, and produced as described in Example 1. Control mice were injected with PBS vehicle only. Experimental and control mice were injected daily for 36 days, after which tumor volume was determined using standard methods.

Figure 4:
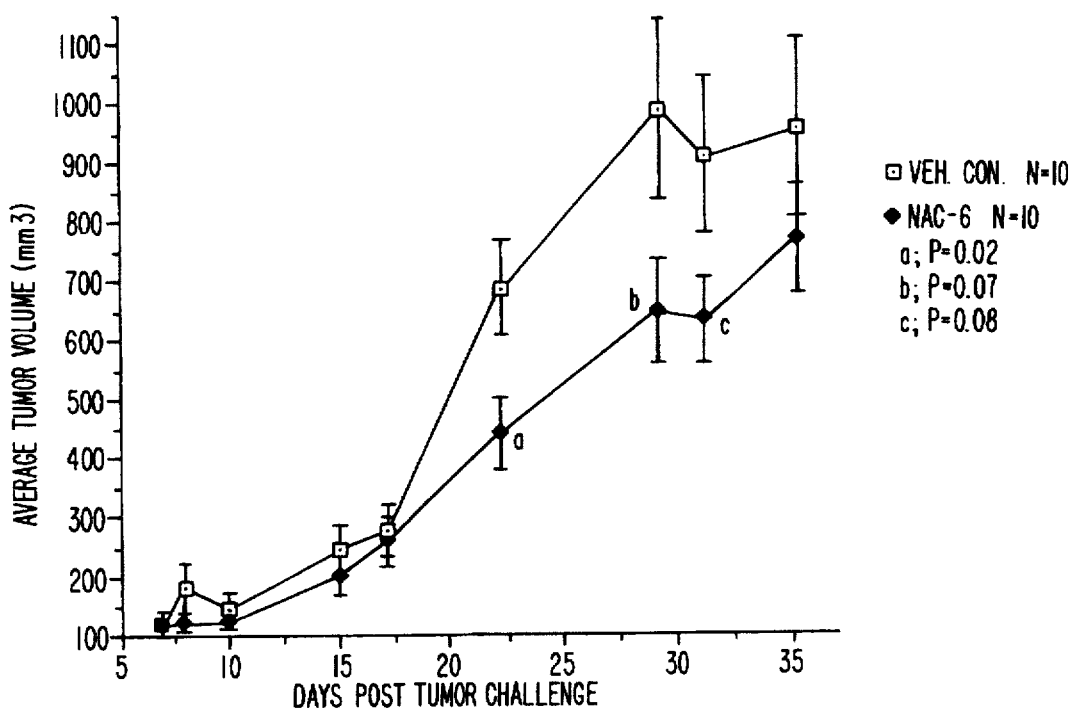
FIG. 4 shows the anti-tumor activity of 2-O, 3-O desulfated heparin in nude mice on the highly metastatic pancreatic adenocarcinoma tumor cell line, CAPAN.

The results are shown in FIG. 4. It is apparent that there is significant anti-tumor activity of the 2-O, 3-O desulfated heparin composition, denoted NAC 6 in the figure, starting at about day 20, and continuing to day 31 post tumor challenge.

Similar experiments were conducted in nude mice using the mammary adeno-carcinoma, MDA231, cell line. Mice were dosed at 50 mg/kg/day. The results revealed that 2-O, 3-O desulfated heparin composition significantly inhibited the growth of the tumor cells.

EXAMPLE 17

Effect of Sodium Hydroxide Concentration on the Production of 2-O, 3-O Desulfated Heparin Fragments Experiments were conducted using heparin fragments to show that the extent of 2-O, 3-O desulfation of such fragments is a function of the concentration of sodium hydroxide used to carry out the reaction. In previous experiments this was shown for substantially undepolymerized heparin.

The materials and methods used were essentially those set forth in the relevant preceding examples. Note though that 2.0 g of low molecular weight (3 Kd) hog mucosal heparin was used for the experiments. Table 2 lists certain of the reaction conditions including the concentrations of sodium hydroxide, yield of the reaction products, % APTT, and disaccharide analysis. The latter two parameters are plotted in FIG. 5 as function of sodium hydroxide concentration.

Figure 5:
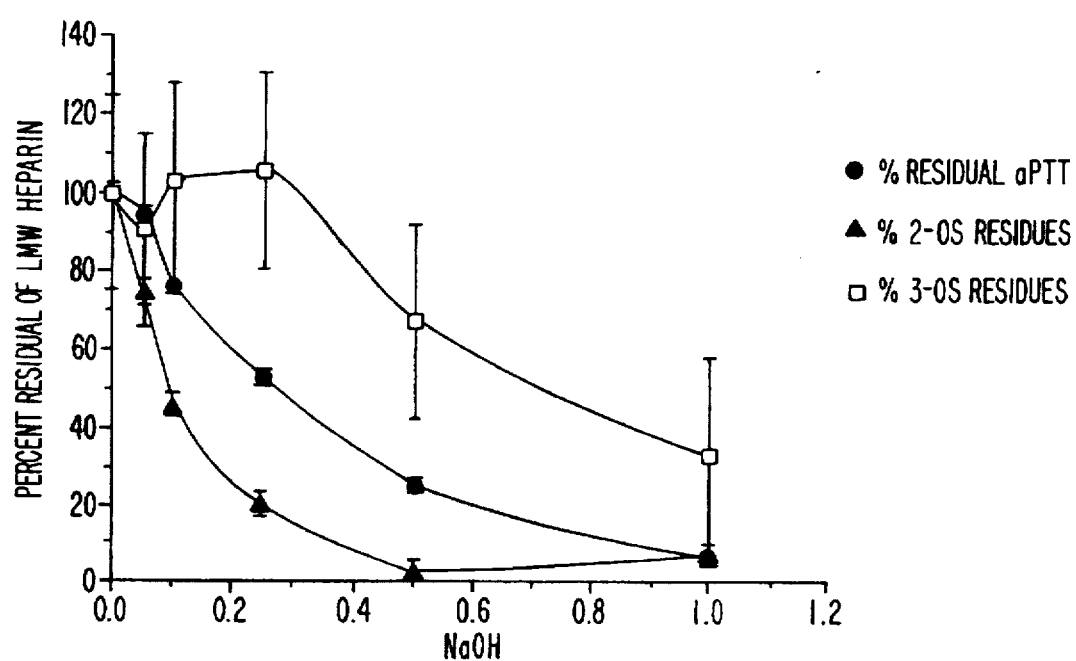
FIG. 5 shows the effect of sodium hydroxide concentration on 2-O, 3-O desulfation of heparin fragments.

From FIG. 5 it is apparent that APTT activity of the reacted fragments relative to control low molecular weight heparin gradually declines over the concentrations of sodium hydroxide tested, and approaches zero at about 1M sodium hydroxide. Measurements of the level of 2-O, 3-O sulfation of the fragments revealed a greater loss of 2-O sulfate residues at lower sodium hydroxide concentrations than that observed for 3-O sulfate residues with nearly total 2-O desulfation at sodium hydroxide concentrations of 0.5M or greater. Over the same concentration of sodium hydroxide, more 3-O sulfate residues were maintained than 2-O sulfate residues, but as shown in the figure at 1M sodium hydroxide only 30–35% of the original 3-O sulfate resides present in the 3 Kd fragments are maintained.

Having described what the applicants believe their invention to be, a skilled practitioner of this art should not construe the invention to be limited other that by the scope of the appended claims.

We claim:

1. A composition comprising unfragmented 2-O, 3-O desulfated heparin, or 2-O, 3-O desulfated heparin fragments wherein said unfragmented 2-O, 3-O desulfated heparin, or 2-O, 3-O desulfated heparin fragments are from 80% to 99% and from 24% to 75% desulfated at the 2-O and 3-O positions, respectively, and wherein said 2-O, 3-O desulfated heparin fragments have an average molecular weight range of 2–6.5 kd.

2. The composition of claim 1 wherein said composition comprises said 2-O, 3-O desulfated heparing fragments.

3. The composition of claim 2 wherein said fragments have an average molecular weight range of about 5 kd.

4. A pharmaceutical composition comprising unfragmented 2-O, 3-O desulfated heparin, or 2-O, 3-O desulfated heparin fragments wherein said unfragmented 2-O, 3-O desulfated heparin, or 2-O, 3-O desulfated heparin fragments are from 80%. to 99% and from 24% to 75% desulfated at the 2-O and 3-O positions, respectively, and wherein said 2-O, 3-O desulfated heparin fragments have an average molecular weight range Of 2–6.5 kd.

5. The pharmaceutical composition of claim 4 wherein said composition comprises said 2-O, 3-O desulfated heparing fragments.

6. The pharmaceutical composition of claim 4 wherein said unfragmented 2-O, 3-O desulfated heparin or 2-O, 3-O desulfated heparin fragments have art average molecular weight range of about 5 kd.

7. The composition of claim 1, wherein said 2-O, 3-O desulfated heparin fragments are about 65% desulfated at the 3-O position.

8. The composition of claim 7 wherein said composition has APTT activity of about 10% of heparin.

9. A composition comprising unfragmented 2-O, 3-O desulfated heparin or 2-O, 3-O desulfated heparin fragments that are from 80% to 99% and from 24 % to 75 % desulfated at the 2-O and 3-O positions, respectively, and wherein said 2-O, 3-O desulfated heparin fragments have an average molecular weight range Of 2–6.5 kd, prepared by:

a) admixing in solution heparin or heparin fragments and an amount of bivalent metal cation that is sufficient to produce the desired amount of desulfation, said solution having an alkaline pH; and b) freezing and lyophilizing said solution.

10. The composition of claim 9 wherein said alkaline pH is from 11–14.

11. The composition of claim 10 wherein said pH is 13.

12. The composition of claim 11, wherein a reducing agent is added to said solution in step a).

* * * * *